United States Patent [19]

Langer

[11] 4,254,775

[45] Mar. 10, 1981

[54] IMPLANTABLE DEFIBRILLATOR AND PACKAGE THEREFOR

[75] Inventor: Alois A. Langer, Pittsburgh, Pa.

[73] Assignee: Mieczyslaw Mirowski, Owings Mills, Md.

[21] Appl. No.: 53,797

[22] Filed: Jul. 2, 1979

[51] Int. Cl.³ ............................................. A61N 1/36
[52] U.S. Cl. ......................... 128/419 D; 128/419 PS
[58] Field of Search .......... 128/419 P, 419 PS, 419 D

[56] References Cited

U.S. PATENT DOCUMENTS

| | | | |
|---|---|---|---|
| 3,649,367 | 3/1972 | Purdy | 128/419 PS |
| 3,822,707 | 7/1974 | Adducci | 128/419 PS |
| 3,857,398 | 12/1974 | Rubin | 128/419 D |
| 3,888,260 | 6/1975 | Fischell | 128/419 PS |
| 3,918,460 | 11/1975 | King et al. | 128/419 P |
| 3,924,640 | 12/1975 | King | 128/419 P |
| 3,926,198 | 12/1975 | Kolenik | 128/419 PS |
| 3,957,056 | 5/1976 | Comben et al. | 128/419 P |
| 4,041,956 | 8/1977 | Purdy et al. | 128/419 PS |

Primary Examiner—William E. Kamm
Attorney, Agent, or Firm—Fleit & Jacobson

[57] ABSTRACT

A fully implantable defibrillator in which the components of the defibrillator are housed within an implantable casing. Defined within the implantable casing are two chambers. Each of the chambers is hermetically sealed from the other and from the exterior environment surrounding the implantable casing. Disposed within the first chamber is a battery and an energy storage device. A charging circuit is disposed within the second chamber and is operatively associated with the battery and the energy storage device for charging the energy storage device to a level capable of defibrillating a malfunctioning heart. A discharging circuit is disposed within the second chamber and is operatively associated with the energy storage device, for initiating the discharge of the energy storage device into the heart of the wearer. The geometry of the implantable casing is chosen to optimize the packaging of the defibrillator components therein.

29 Claims, 8 Drawing Figures

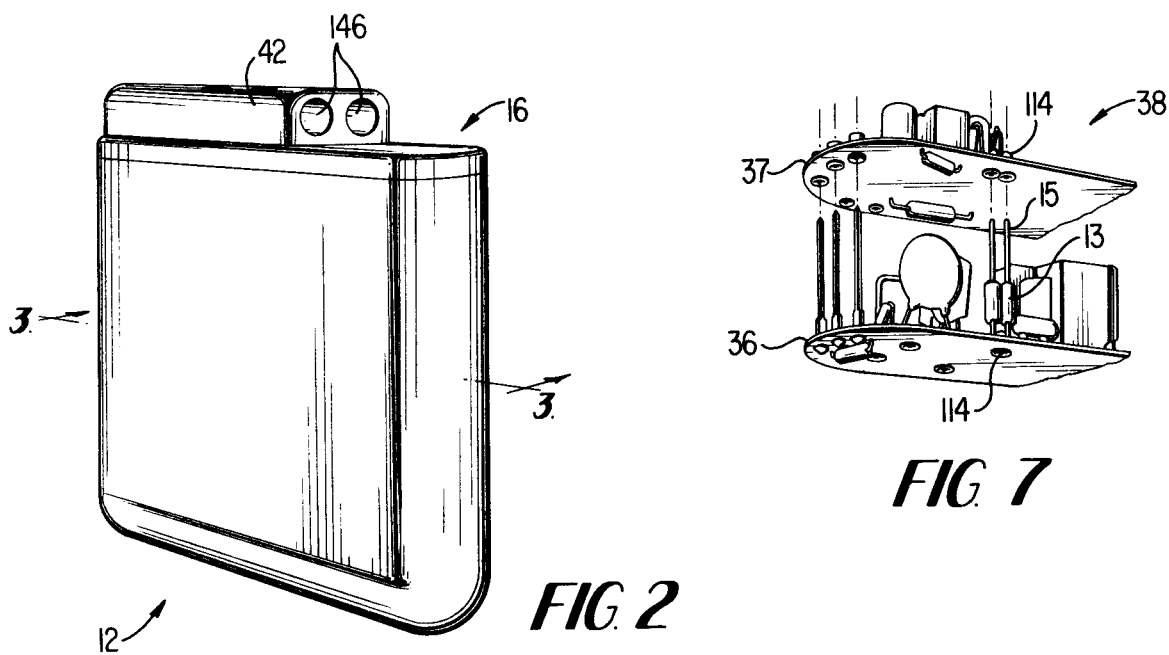
FIG. 2
FIG. 7
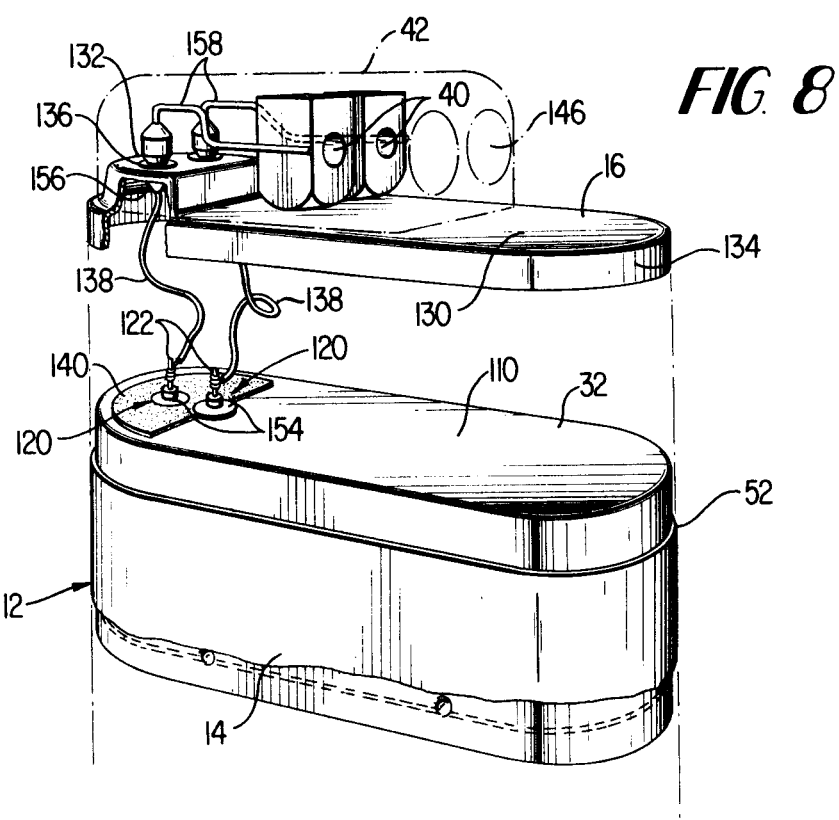
FIG. 8

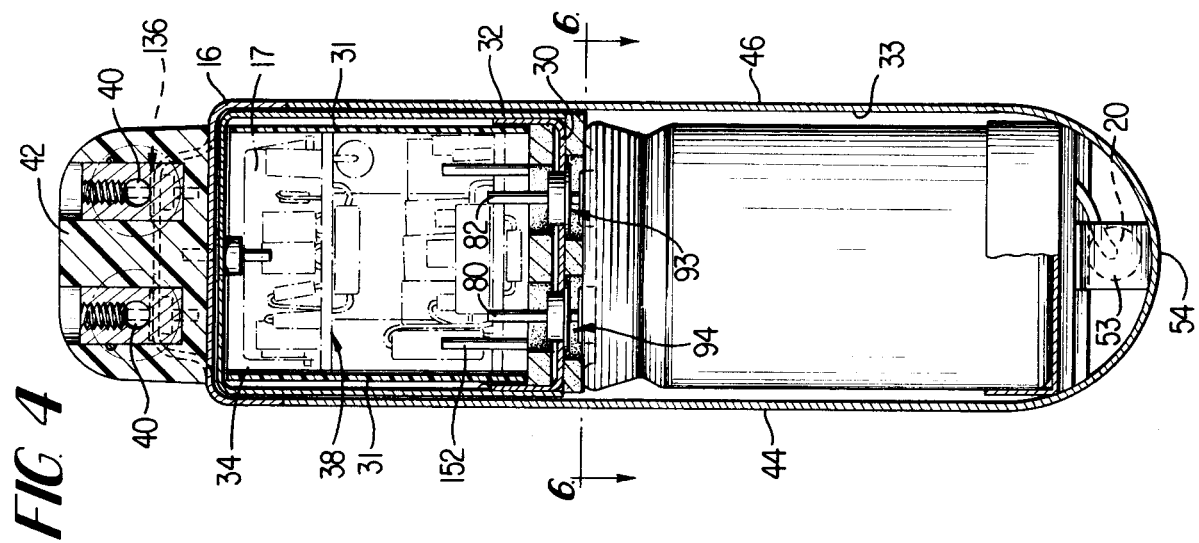
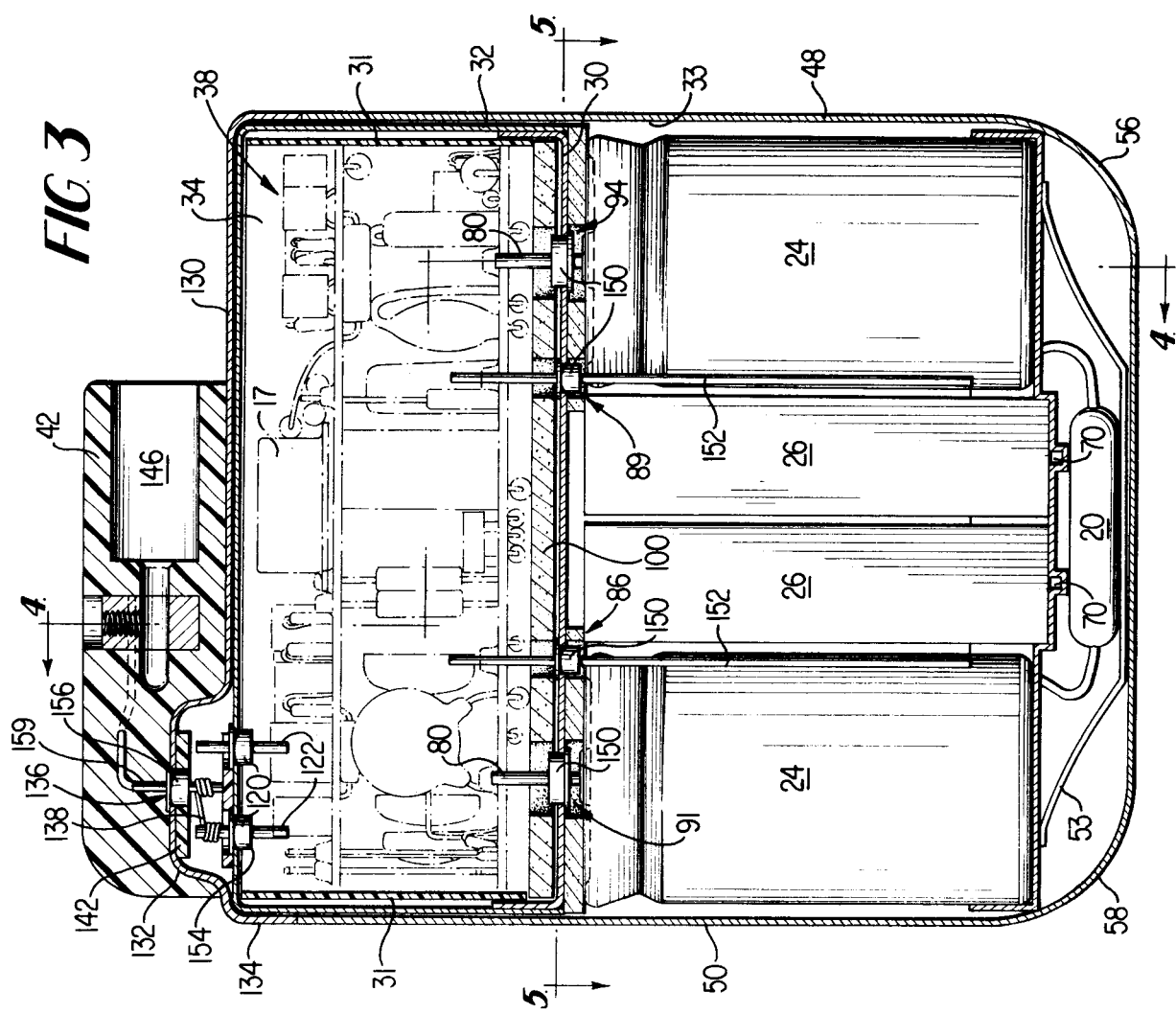

IMPLANTABLE DEFIBRILLATOR AND PACKAGE THEREFOR

BACKGROUND OF THE INVENTION

1. Field of the Invention

This invention relates to the packaging of implantable life-assisting devices, in general, and to the packaging of a fully implantable defibrillator, in particular.

2. Description of The Prior Art

Great strides are presently being made to develop an automatic, fully implantable defibrillator. See, for example, U.S. Pat. Nos. Res. 27,652 and 27,757, where the first concept of the automatic implantable ventricular defibrillator is described. Recent advances have also been made in enhancing the reliability of fibrillation detectors. In this latter regard, see U.S. Pat. Nos. 4,184,493 and 4,202,340. Furthermore, as outlined in U.S. Pat. No. 4,164,946 steps have been taken to improve the reliability of the implanted defibrillator by the provision of circuitry, which interrogates the implanted electronics to verify proper operation before a difibrillating shock is delivered.

Notwithstanding the substantial steps which have been taken to develop the automatic, fully implantable defibrillator and to ensure the operation of the sensing and defibrillating circuitry, it must not be forgotton that the implantable defibrillator is in its infacy. Since implantable defibrillators are positioned within the body, small size is an essential characteristic. Also essential is the insulation of defibrillator components from corrosive attack by the biological fluids surrounding the defibrillator at the implant site, and the protection of the defibrillator components from attack by other components, such as the energy storage devices, should these latter components begin to release gases and fluids.

The present invention is directed toward filling the needs expressed above.

SUMMARY OF THE INVENTION

The subject invention relates to a fully implantable defibrillator in which the components of the defibrillator are housed within an implantable casing. Defined within the implantable casing, or housing, are two chambers, each of which is hermetically sealed from the other and from the exterior environment surrounding the implantable casing. Disposed within the first chamber is a battery and an energy storage device. A charging circuit, disposed within the second chamber, is operatively associated with the battery and the energy storage device for charging the energy storage device to a level capable of defibrillating a malfunctioning heart. A discharging circuit, disposed within the second chamber, is operatively associated with the energy storage device for initiating the discharge of the energy storage device into the heart of the wearer. The geometry of the implantable casing is chosen to optimize the packaging of the defibrillator components therein.

It is thus an object of the present invention to provide a compact implantable defibrillator, which is structured to isolate susceptible defibrillator components from components which could have an adverse effect on defibrillator operation, and to isolate all implanted components from the detrimental effects of biological fluids present at the implant site.

It is another object of the present invention to provide an implantable defibrillator which is hermetically sealed from the body cavity of a recipient so that the defibrillator is protected from the effects of biological liquids and gases in the body cavity.

It is a further object of the present invention to provide an implantable defibrillator in which the electronics of the defibrillator are protected from gases which could be released by the defibrillator's energy storage devices.

It is still an object of the present invention to provide a package for an implantable defibrillator, the package being electrically isolated from the electronics associated with the defibrillator.

It is a further object of the present invention to provide a package of minimum size for an implantable defibrillator.

It is yet another object of the present invention to provide an implantable defibrillator housed in a package which enhances patient comfort and minimizes internal bruising of the patient at the implant site.

It is still another object of the present invention to provide a metal casing hermetically sealing the interior zones of an implantable defibrillator from exposure to body fluids in the cavity in which the defibrillator is implanted.

It is yet a further object of the present invention to provide an implantable defibrillator containing a hermetically sealed battery-capacitor chamber and a hermetically sealed circuitry chamber.

It is still a further object of the present invention to provide an implantable defibrillator in which the electronic components may be easily and quickly attached and detached from each other.

Other objects and advantages of this invention will further become apparent when reference is made to the following description and to the accompanying drawings.

BRIEF DESCRIPTION OF THE DRAWINGS

FIG. 2, is a perspective of the assembled package of FIG. 1;

FIG. 3, is a sectional view of the package as viewed along lines 3—3 of FIG. 2;

FIG. 4, is a sectional view of the package as viewed along lines 4—4 of FIG. 3;

FIG. 7, is a perspective of part of the printed circuit boards to show how they interconnect; and FIG. 8, is an exploded perspective of the top portion of the package of FIG. 1.

DETAILED DESCRIPTION OF THE DRAWINGS

Figure 1:
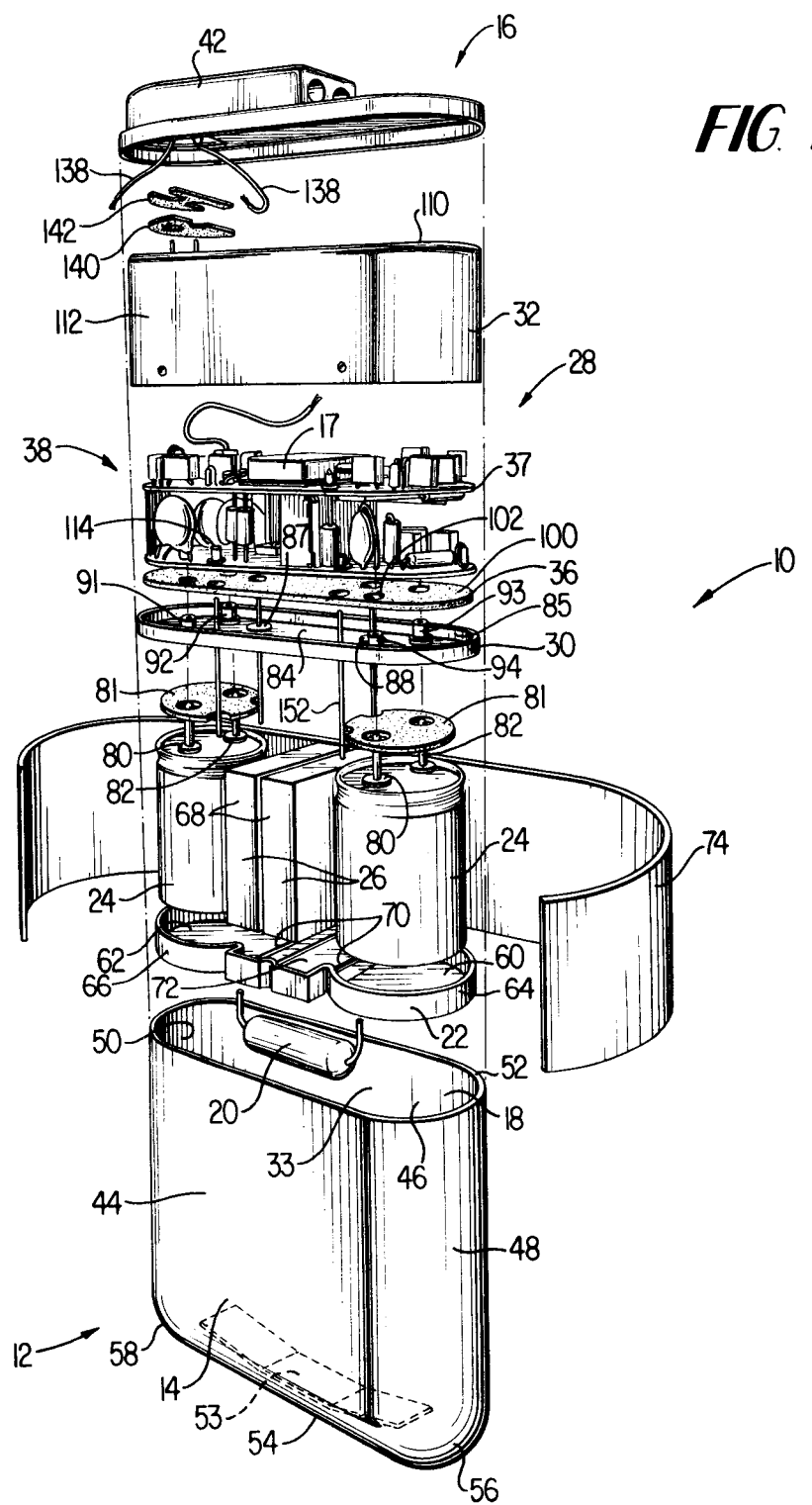
FIG. 1, is an exploded perspective of an embodiment of the implantable defibrillator package according to the teachings of the subject invention.

With reference to FIGS. 1 and 2, the implantable defibrillator, generally designated as 10, includes an outer case 12 having a bottom portion 14 and a lid portion 16. When the lid and the body of the outer case 12 are joined together in a manner described hereinafter, they form a hermetically sealed chamber 18. As viewed in FIG. 1, the bottom of the chamber 18 contains a test load resistor 20. Positioned within the chamber 18 and above the resistor 20 is an insulator 22, and contained within positions provided in the insulator 22 are a pair of cylindrical capacitors 24 and a pair of hermetically sealed batteries 26 arranged one next to the other in a straight line.

Within the case 12, and above the battery-capacitor arrangement, is positioned an inner case 28, which comprises a lid 30 and body portion 32. When the lid 30 and the body portion 32 of the inner case 28 are joined together in a manner described hereinafter, they form a second hermetically sealed chamber 34. Housed within the chamber 34 is a pair of printed circuit boards 36 and 37, which contain the implantable defibrillator's logic circuitry, generally designated as 38. For purposes of the preferred embodiment, logic circuitry 38 takes the form of the defibrillator circuitry disclosed in the aforementioned patents. A conformal coating 31, such as molded selastic preform, acts to bind the printed circuit boards 36 and 37 against the inner case 28 to prevent any unwanted motion of the boards within the inner case.

For purposes of this discussion, the logic circuitry 38 comprises a fibrillation detector circuit, a charging circuit for charging the capacitors 24 to a level capable of defibrillating a malfunctioning heart, and discharging circuitry, responsive to the detection of fibrillation, for initiating the discharge of the charged capacitors 24 into the heart of a wearer.

On the top of lid 16 there are a pair of electrode terminals 40, which are contained within a epoxy-molded portion 42. The electrode terminals provide a means to which are connected the free ends of a pair of implanted leads (not shown), which have been inserted into a heart. These leads perform two functions: the transmission of ECG signals from the heart to the defibrillator, and the transmission of a defibrillating shock from the defibrillator to the heart. As will be described in greater detail hereinafter, the defibrillator contains additional structure for operatively associating the defibrillator logic circuits 38 with the capacitors 24, batteries 26, and electrode terminals 40.

When assembled, the hermetically sealed outer case 12 of the implantable defibrillator 10 ensures that none of the biological fluids and gases present at the implant site are permitted to enter the chamber 18. In like manner, hermetically sealed case 12 prevents any fluids or gases which could be released by the capacitors 24 from entering the human body. Specifically, the hermetically sealed inner case 28 isolates the logic circuits 38 from the capacitors 24, which are not, themselves, hermetically sealed.

A detailed description of a preferred embodiment will now be provided with reference to FIGS. 1, 3 and 4. The outer case 12 is typically made from titanium to assure adequate inertness to biological fluids and gases at the implant site. The case 12 comprises a body 14 which is preferably seamless in nature, and is produced by any of the well-known extrusion processes. Body 14 is defined by a pair of substantially parallel planar wall portions 44 and 46, which merge at their sides in cylindrically curved portions 48 and 50. The walls 44 and 46 and the curved portions 48 and 50 define a peripheral ledge 52. The other end of walls 44 and 46 are joined by a curved portion 54. The curved portion 54 merges in a smooth and continuous fashion with the curved sides 48 and 50 at corner portions 56 and 58.

The overall shape of the outer case 12 is designed to accomplish two purposes. The first is to provide a compact case of minimal size for housing the components and assemblies therein; the second is to provide an exterior configuration relatively devoid of sharp edges to prevent internal bruising of the wearer at the implant site.

Typically, the first component placed within the chamber 18 of the housing 12 is a test load resistor 20, which, as viewed in FIGS. 1, 3 and 4, is received in the case in cradling relationship with the interior wall of curved portion 54. A filling material (not shown) is then introduced into the chamber 18 to a height sufficient to just cover the test load resistor 20. The filling material is typically epoxy filled with glass microspheres, although silicon rubber and foam elastomer can also be used.

On top of the resistor 20 within the casing 12, there is placed an insulator 22. The insulator 22, which is a vacuum-formed component made of a suitable plastic, contains two well regions 60 and 62 defined by walls 64 and 66, respectively, for receiving the cylindrical capacitors 24 which are typically of the aluminum hydrolyte type. The walls 64 and 66 define a region which provides a snug fit for the bottoms of the capacitors 24 within the insulator 22. When in place, the capacitors 24 provide a space between themselves for containing the batteries 26. The batteries 26 are of the lithium anode type, are hermetically sealed, and are individually insulated by being wrapped in a high dielectric tape 68. The insulator 22 contains a pair of recesses 70, and a generally planar top surface 72 for receiving and supporting the batteries 26.

When assembled, the capacitors 24, batteries 26, and insulator 22 are wrapped in a plastic tape 74. The tape 74, which typically has a high dielectic, performs an insulating function between the interior wall of the body 14 and the capacitors 24 and batteries 26. The placement of the batteries 26 and the capacitors 24, as well as the configuration of the body 12, have been carefully chosen to provide a compact housing structure for these components in which the body 12 surrounds and supportively contacts the cell-capacitor arrangement. No space is lost since the rounded edges 48 and 50 conform to and mate with the cylindrical surfaces of the capacitors 24. Any dangers of battery leaking, venting or releasing of gases is minimized through the use of hermetically sealed batteries, which, as stated before, are wrapped in insulating tape 68. Further, the inner surface of the chamber 18 is covered with a suitable film or coating 33 that acts as a hydrogen getter to absorb any of the hydrogen which could be released from the capacitors 24.

The specific structure and contents of the inner case 28 will now be described. As viewed in FIGS. 1, and 3 through 5, the inner case 28 contains a lower lid 30 having a peripheral contour similar to that of the interior wall of the outer case 12. Contained within the peripheral boundary of the lid is a relatively planar portion 84. A wall portion 85 extends upwardly from the base portion 84 about the periphery of the lid. Disposed on the base portion 84 are four solid feed-throughs 86–89 and four tubular feed-throughs 91–94. All of the feed-throughs include an insulator member 150 to provide a hermetic sealing between the chamber 34 inside the inner case 28 and the chamber 18 within the outer case 12. Each of feed-throughs 86–89 contains a wire, or pin, 152 passing therethrough and extending a predefined distance within the chamber 34 of the inner case 28, and into the outer chamber 18 of the outer case 12. The positive lead of batteries 26 is connected to the wire of feed-through 87, while the negative lead of battery 26 is connected to the wire of feed-through 88. The resistor 20 is operatively connected to the wires of feed-throughs 86 and 89. A substantially planar insulator 100 sits on top of the base 84. The insulator 100 contains a plurality of apertures 102 which are configured to allow the insulator 100 to lie on the base surface 84 with the feed-throughs extending therethrough.

The inner case 28, typically made from cupro-nickel alloy, is defined by a substantially planar top portion 100 and a wall portion 112, which extends a predefined distance, as viewed in FIG. 1, downwardly from and about the periphery of the top portion 110. The lid 30 is press-fit into the body portion 32 of inner case 28 to define an inner chamber 34. The inner case 28 is then welded along the area where the lid 30 meets the body portion 32 to hermetically seal the chamber 34. The configuration of the inner case 28 has been chosen to provide a snug fit between the exterior surface of wall portion 112 and the interior surface of the outer case 12. Contained within the inner chamber 34 are the defibrillator logic circuits 38, which are disposed on printed circuit boards 36 and 37. Sockets 114 are provided on the bottom of the circuit boards. When the printed circuit boards 36–37 are placed on top of the insulator 100, the wires extending from the solid feed-throughs 86–89 are received in corresponding sockets on printed circuit board 36. With reference to FIGS. 3 and 4, a molded silastic preform 31 acts to provide a snug fit for the printed circuit boards within the inner case to prevent unwanted motion of the boards within the inner case.

The printed circuit boards 36 and 37 are arranged so that they may be quickly and easily attached to and detached from each other. This is accomplished by providing pins and mating sockets on each of the boards; it is contemplated that this connecting arrangement may be part of the operative circuitry of the logic circuits 38. For example, in FIG. 7, notice that resistor 13 terminates in a pin 15, which is frictionally engaged in socket 114. Likewise, certain of the integrated circuit chips, for example, chip 17 in FIG. 1, may be mounted through a similar arrangement of pins and sockets.

Figure 5:
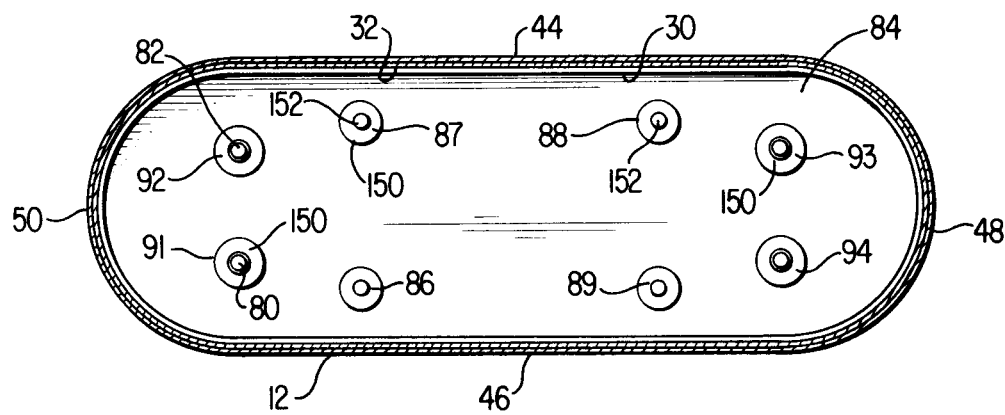
FIG. 5, is a sectional view of the package as viewed along lines 5—5 of FIG. 3.
Figure 6:
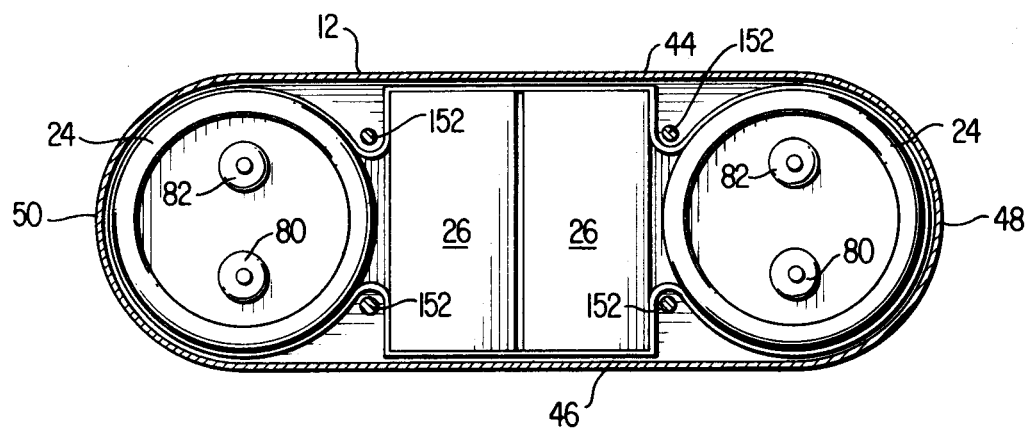
FIG. 6, is a sectional view of the package as viewed along lines 6—6 of FIG. 4.

When assembled, the inner case 28 provides a hermetically sealed chamber for housing the defibrillator logic circuits 38. As best seen in FIGS. 1, 5 and 6, the inner case 28 is received in the outer case 12 so that the anode pins 80 and cathode pins 82 extending from capacitors 24 pass through the tubular feed-throughs 91–94 to make connection with mating sockets on printed circuit boards 36 and 37. Between each capacitor 24 and the bottom of lid 30 is a disc-shaped insulator 81. A leaf spring 53, positioned within the bottom of the chamber 18, acts to constantly urge the capacitors 24 toward the bottom of lid 30 to maintain the connection between the pins, 80 and 82 and the mating sockets on printed circuit boards 36. The placement of the inner case within the outer case 12 completes the assembly of the components within the defibrillator 10.

With reference to FIGS. 3, 4 and 8, the top portion 110 of the inner case 28 contains a pair of feed-throughs 120. Extending through these feed-throughs are leads 122. The portions of the leads 122 extending into the chamber of the inner case 28 are operatively connected to the logic circuits 38. The other ends of the leads 122 extend a predefined distance out of the top surface 110. The feed-throughs 120 contain an insulator member 154 to provide a hermetic seal.

The lid 16 of the outer case 12 contains a substantially planar top portion 130, which contains an outwardly extending embossed area 132. A wall portion 134 extends downwardly from and about the periphery of the top portion 130. The wall portion 134 of the lid 16 is configured such that an abutting relationship is created between the end of the wall portion 134 and the ledge 52 of the outer case 12. The butt joint between the lid 16 and the body 14 is effected by a conventional welding process to ensure that the chamber created within the outer case 12 is hermetically sealed. Contained on the embossed area 132 are a pair of feed-throughs 136, which contain an insulating member 156 to provide a hermetic seal. Each of the feed-throughs contains a wire lead 158 extending therethrough. The portion of each lead extending into the chamber 18 of the outer case 12 is connected by means of a spring wire 138 to one of the leads 122 extending out of feed-through 120. The portions of the leads 158 extending out of the embossed area 132 are connected to the rigidly positioned electrode terminals 40. Insulators 140 and 142 are interposed between the top surface 110 of the inner case 28 and the bottom surface of the lid 16 to prevent any contact between the portions of these members and the spring wires 138. An epoxy form 42 completely covers the embossed area and electrode terminals of lid 16, and further defines sockets 146 for receiving the free ends of the leads which are associated with the heart.

Obviously, many modifications and variations of the present invention are possible in light of the above teachings, and it is contemplated that the sizes of the various components may be altered, to further reduce the overall size of the defibrillator package, and to provide for the addition or subtraction of the printed circuit boards within the inner case. It is further contemplated that within the scope of the appended claims, the invention may be practiced otherwise than as specifically described.

I claim:

1. A cardioverter fully implantable in the body of a recipient, said cardioverter comprising:

an outer casing;

first and second chambers within said outer casing, each of said chambers being hermetically sealed from the other, and being hermetically sealed from the exterior environment surrounding said casing;

battery means and energyy storage means disposed within said first chamber;

electrode terminal means disposed on said outer casing; and defibrillator logic circuitry disposed within said second chamber and operatively associated with said electrode terminal means, said battery means and said energy storage means for charging said energy storage means to a level capable of defibrillating a malfunctioning heart, and for initiating the discharge of said energy storage means into the heart of said recipient.

2. The cardioverter of claim 1, wherein said first chamber is defined by said outer casing, and further comprising an inner casing disposed within said first chamber, said inner casing defining said second chamber.

3. The cardioverter of claim 2, wherein said outer casing contiguously surrounds and supportively contacts said inner casing.

4. The cardioverter of claim 1, wherein said outer casing is made from a material which is inert to biological fluids.

5. The cardioverter of claim 4, wherein said material is titanium.

6. The cardioverter of claim 1, further comprising interconnecting means maintaining the hermetic seal between chambers for interconnecting said defibrillator logic circuitry with said battery means and said energy storage means.

7. The cardioverter of claim 5, wherein said interconnecting means comprises a plurality of electrical insulators mounted on said second case, and wire leads passing through said insulators to accomplish said interconnections.

8. The cardioverter of claim 1, further comprising means for hermetically sealing said battery means.

9. The cardioverter of claim 1, wherein said battery means is a plurality of cells, and said energy storage means is a pair of cylindrical capacitors.

10. The cardioverter of claim 9, wherein said cells and said capacitors are disposed one next to the other in a straight line.

11. The cardioverter of claim 9, wherein said cells are disposed between said capacitors.

12. The cardioverter of claim 10, wherein the dimensions of said outer casing are chosen so that the outer casing surrounds and supportively contacts said cell-capacitor arrangement.

13. The cardioverter of claim 1, further comprising electrode means electrically connected to said electrode terminal means for operatively associating said cardioverter with said heart.

14. The cardioverter of claim 13, wherein said electrode terminal means comprises a pair of electrode terminals disposed on said outer casing, each of said terminals being electrically insulated from said outer casing, and wherein said electrode means comprises a pair of leads for connecting said electrode terminals to said heart.

15. The cardioverter of claim 1, wherein said defibrillator logic circuitry comprises charging circuitry for charging said energy storage means to a level capable of defibrillating a malfunctioning heart, and discharging means for initiating the discharge of said energy storage means into the heart of said recipient.

16. The cardioverter of claim 1, further comprising means for electrically isolating from each other said logic circuitry in said second chamber, said battery and energy storage means in said first chamber, and the body of said recipient.

17. The cardioverter of claim 16, wherein said isolating means comprising a high dielectric film associated with said battery and said energy storage means, and a conformal coating associated with said logic circuitry.

18. A fully implantable cardioverter comprising:
an implantable casing defining a first chamber, said first chamber being hermetically sealed from the exterior environment surrounding said implantable casing;
electrode terminal means disposed on said implantable casing;
a pair of capacitors;
a battery disposed between said pair of capacitors;
said battery-capacitor arrangement disposed within said first chamber so that said implantable casing surrounds and supports said arrangement;
an inner casing disposed within said first chamber adjacent said arrangement, said inner casing defining a second chamber, said second chamber being hermetically sealed from said first chamber and from the exterior environment surrounding said implantable casing; and
logic circuitry disposed within said second chamber and operatively associated with said electrode terminal means, said battery, and said pair of capacitors for charging said capacitors to a level capable of defibrillating a malfunctioning heart, and for initiating the discharge of said capacitors preparatory to deliverance of defibrillating energy into said heart.

19. The cardioverter of claim 18, further comprising first insulating means for electrically insulating said arrangement from said implantable casing.

20. The cardioverter of claim 18, further comprising second insulating means for electrically insulating said arrangement from said inner casing.

21. The cardioverter of claim 18, further comprising logic means disposed in said second chamber for carrying out the functions associated with said cardioverter.

22. The cardioverter of claim 18, further comprising third insulating means for electrically insulating said logic means from said inner casing.

23. A cardioverter fully implantable in the body of a recipient, said cardioverter comprising:
a housing having a continuous wall structure, said housing being open at one end, and said wall structure defining two opposed cylindrically shaped portions;
lid means secured to the open end of said housing for creating a chamber within said housing, said chamber being hermetically sealed from the exterior environment of said housing;
lead-receiving means secured to said lid means for providing an external attachment point to operatively associate said cardioverter with said heart;
battery means disposed within said housing;
energy storage means including a pair of cylindrical capacitors;
means for positioning said capacitors so that a portion of the cylindrical surface of each one of said capacitors mates with and is supported by a corresponding one of said two opposed cylindrically shaped portions; and
defibrillator logic circuitry disposed within said housing and operatively associated with said lead-receiving means, said battery means and said energy storage means for charging said energy storage means to a level capable of defibrillating a malfunctioning heart, and for initiating the discharge of said energy storage means into the heart of said recipient.

24. The cardioverter of claim 23, further comprising hydrogen getter means within said housing.

25. The cardioverter of claim 23, wherein said lead-receiving means comprises an epoxy form secured to said lid, and a pair of lead-receiving sockets defined in said epoxy form.

26. A cardioverter fully implantable in the body of a recipient, said cardioverter comprising:
a housing hermetically sealed from the exterior environment surrounding said housing;
electrode terminal means disposed on said housing;
battery means and energy storage means disposed within said housing; and defibrillator logic circuitry disposed within said housing and operatively associated with electrode terminal means, said battery means and said energy storage means for charging said energy storage means to a level capable of defibrillating a malfunctioning heart, and for initiating the discharge of said energy storage means into the heart of said recipient, said defibrillator logic circuitry comprising a plurality of printed circuit boards, a plurality of circuit elements mounted on said boards, and connecting means for quick and easy attachment and detachment of said boards to each other, and to said battery means and energy storage means.

27. The cardioverter of claim 26, wherein said connecting means comprises
a plurality of pins; and
a plurality of sockets, each of said sockets frictionally engaging one of said pins, said pins and sockets being disposed on different of said printed circuit boards so that each of said sockets frictionally engages one of said pins.

28. The cardioverter of claim 26, wherein said connecting means is electrically conductive and wherein said cardioverter further comprises means for electrically connecting certain of said circuit elements to said connecting means.

29. The cardioverter of claim 26, wherein said connecting means comprises pins forming part of and defining connection points for said battery means and said energy storage means, and tubular sockets secured to certain of said printed circuit boards, each of said sockets frictionally engaging one of said pins.

* * * * *